(12) United States Patent
Al Mohizea

(10) Patent No.: US 8,403,863 B2
(45) Date of Patent: Mar. 26, 2013

(54) MODIFIED BIOPSY DEVICE

(76) Inventor: Saad Ibrahim Al Mohizea, Riyadh (SA)

( * ) Notice: Subject to any disclaimer, the term of this patent is extended or adjusted under 35 U.S.C. 154(b) by 178 days.

(21) Appl. No.: 12/780,010

(22) Filed: May 14, 2010

(65) Prior Publication Data

US 2011/0282240 A1 Nov. 17, 2011

(51) Int. Cl.
*A61B 10/00* (2006.01)
(52) U.S. Cl. ......... 600/566; 600/564; 600/567; 606/184
(58) Field of Classification Search .......... 600/564–566, 600/562, 567, 568; 606/167, 170, 184
See application file for complete search history.

(56) References Cited

U.S. PATENT DOCUMENTS

| | | | | |
|---|---|---|---|---|
| 5,425,376 A | * | 6/1995 | Banys et al. | 600/566 |
| 2005/0165328 A1 | * | 7/2005 | Heske et al. | 600/566 |
| 2009/0253998 A1 | * | 10/2009 | Chen | 600/565 |

* cited by examiner

*Primary Examiner* — Brian Szmal
*Assistant Examiner* — Emily Lloyd

(57) ABSTRACT

A biopsy device for excising tissue from skin and hair comprising a syringe for numbing the area to be excised coupled to a sleeve mounted on the exterior of the syringe with a blade attached to the distal edge of the sleeve. The sleeve is manually slidable from an extended position where the needle is retracted within to a retracted position where the needle is exposed.

14 Claims, 3 Drawing Sheets

24 23 1 3

2   1   25   23 ise behind. Furthermore, due to the curved shape of the blades, the blades may fail to completely cut the tissue.

For those reasons it would be desirable to have an instrument that minimizes the use of multiple sharp objects and eliminates unnecessary steps in a biopsy procedure to reduce the risk for injury that happens when handing over or disposing of contaminated sharp instruments.

This and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

Unless the context dictates the contrary, all ranges set forth herein should be interpreted as being inclusive of their endpoints, and open-ended ranges should be interpreted to include only commercially practical values. Similarly, all lists of values should be considered as inclusive of intermediate values unless the context indicates the contrary.

MODIFIED BIOPSY DEVICE

FIELD OF THE INVENTION

The invention relates to medical devices and more specifically to instruments used for excising tissue for diagnostic or treatment purposes in humans and animals, particularly for cutaneous biopsies.

BACKGROUND

A punch biopsy is diagnostic procedure used for obtaining a tissue specimen for histopathological examination. It is also used for excising tissue and for hair transplantation. Although any organ can be biopsied, punches are commonly used to take biopsies of skin, nail and hair. Punch biopsies are usually done with a simple biopsy punch that includes two members: a handle and a cutting member made of steel. The cutting member is generally a hollow cylinder that is sharp at a lower edge. The area is numbed first with a local infiltration of an anesthetic with a needle. A couple of injections are usually required to cover the whole field. The proper level of injection should be at the upper dermis, which is rich in nerve endings. The procedure is then initiated by pressing and rotating the biopsy punch against the tissue in a coring motion. The biopsy punch then is pulled back, and a needle or tweezers are used to stabilize tissue cut by the biopsy punch. The stabilized tissue then is cut at a base of the tissue with scissors or a blade.

There are negative aspects of the traditional biopsy punch. For example, needles are typically used to expose and stabilize the base of the tissue prior to cutting the base with the scissors or a blade. Needles are also used to dislodge a biopsied specimen from a chamber of the biopsy punch. In such scenarios, doctors are susceptible to accidentally sticking themselves or an assistant with the needle with the risk of contracting infections such as HIV infection.

Additionally, holding the base of the tissue too firmly can compromise the usefulness of the tissue for histopathology reading by creating artifacts that may confuse results. Still further, when the surgeon reaches out for the punch after numbing the patient with the needle, he may forget exactly where was the area he anaesthetized, and may have to inject again if he didn't dispose of the instrument already.

In U.S. Pat. No. 5,325,857 a device comprises a syringe, a detachable needle mounted on one end portion of the syringe, a biopsy punch attached to the same end portion, which is accessible only when the needle is removed. Since the needle has to be removed manually before using the punch this adds an unnecessary step that can endanger the personnel by inadvertent stick injury. U.S. Pat. No. 3,515,128 incorporates a piston that is used to create a vacuum to retain the skin plug within the blade before its final release. However, it still uses a blade to sever the tissue at its base. It also doesn't give any mechanism for utilizing the negative pressure that usually tends to resist and give away before one can sever the tissue. U.S. Pat. No. 3,577,979 attempts to address these problems by using a set of short prongs located inside a cutting member to pierce skin if a biopsy punch is rotated in a direction opposite the direction of the prongs. The short prongs, however, may damage a tissue specimen and do not provide a component to cut the base of the tissue. The short prongs stabilize the tissue for cutting by scissors. U.S. Patent Application Publication No. 2007/0232954 generates elliptical biopsies by oscillating two cutter blades which are curved sideways and flat from top to bottom using a motor drive. The device, however, produces only superficial biopsies, up to 4 mm deep, which leaves part of the dermis and subcutaneous

SUMMARY

The inventive subject matter provides apparatus, systems and methods to overcome the above mentioned drawbacks of the old biopsy punches by reducing the need for additional instrumentation, and the need to reach out for other instruments during the different stages of the procedure especially anesthetizing, cutting the base of the biopsy and dislodging specimens from the interior of the punch.

In one aspect, the instrument comprises two components that are slidably attached to each other, a syringe and a sleeve. At one end of the sleeve at the same side of the needle is a circular blade connected to the sleeve. The two components are made so that the needle projects at the centre of the slidable blade. The sleeve is contiguous with the barrel of the syringe and has the means to slide relative to the barrel of the syringe from a retracted position where the needle is fully exposed and available for injecting anesthetic fluid to an extended position where the needle is hidden and the blade is available for cutting the tissue. Means for locking the instrument in certain positions are optionally installed as will be explained later. In one variation the blade is permanently fixed to the needle assembly with the needle cannula partially exposed for injection.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Various objects, features, aspects and advantages of the inventive subject matter will become more apparent from the following detailed description of preferred embodiments, along with the accompanying drawing figures in which like numerals represent like components.

DETAILED DESCRIPTION

The embodiments described below with reference to the drawings are only examples, and the inventive subject matter should not be construed as being limited by these embodiments. In particular, the inventive subject matter should be construed as including methodologies that have a wide range of uses.

In this description, and for the sake of clarification, proximal end means the end closer to the injector's hand when holding the instrument and performing the procedure, whereas distal end means the end farther away from the injector's hand. A biopsy syringe device is a device that can be used for both numbing the skin and taking the biopsy. A biopsy needle device is similar but with the blade fixed to the needle assembly.

Figures 1, 2:
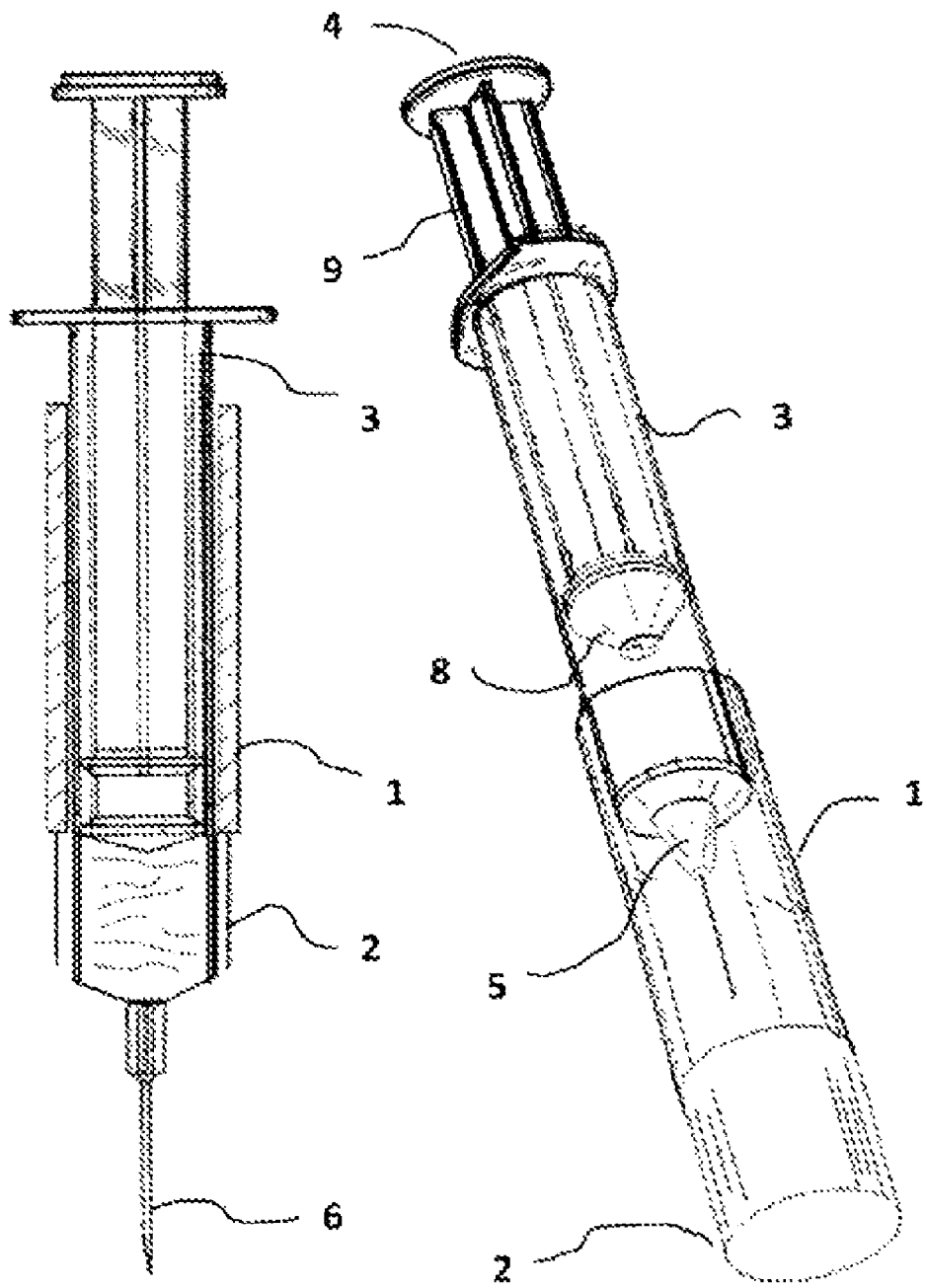
FIG. 1 shows a cross sectional view of an exemplary biopsy device, with the sleeve in a retracted position, according to one aspect of the invention.
FIG. 2 shows a perspective view of an exemplary biopsy device, with the sleeve in an extended position.

In one preferred embodiment, referring to FIGS. 1 and 2, the device is a biopsy syringe comprised of two components, a syringe slidably attached inside a sleeve in an axial axis. The syringe assembly can be of conventional construction. It comprises an elongated barrel 3, a needle assembly and a plunger assembly. The distal end of the barrel is tapered and configured to accommodate the needle assembly comprised of a hub 5 and a needle 6 projecting outwardly.

The barrel receives within its interior a plunger assembly. The plunger assembly comprises an elongated shaft 9 ending in a stopper 8. The shaft's length is longer than the barrel. The plunger is used to push fluid out of the barrel through its communication with the hub 5 and finally through the needle 6. This is accomplished by pressing on the head of the plunger 4 and is assured by the air tight fit assembly of the slidably positioned stopper 8. The diameter of the stopper is just larger than the inside diameter of the barrel 3 and is made preferably from rubber to ensure a tight but flexible fit. The barrel 3 is housed within a sleeve 1. The sleeve has a diameter larger than the barrel's and includes a blade 2 mounted at the distal end. The blade is cylindrical and is sharpened at its distal edge. The blade's diameter can be of different sizes, which corresponds to the biopsy size (usually from 1-8 mm) and the height (usually from 2-20 mm) can also be variable depending on the biopsy location. The sleeve and the barrel can slide easily relative to each other from a position where the needle is fully exposed and ready for injection (FIG. 1) to a position where the needle is housed inside the sleeve with the needle hidden within and the blade projecting and available for cutting the tissue (FIG. 2).

Figures 3A, 3B:
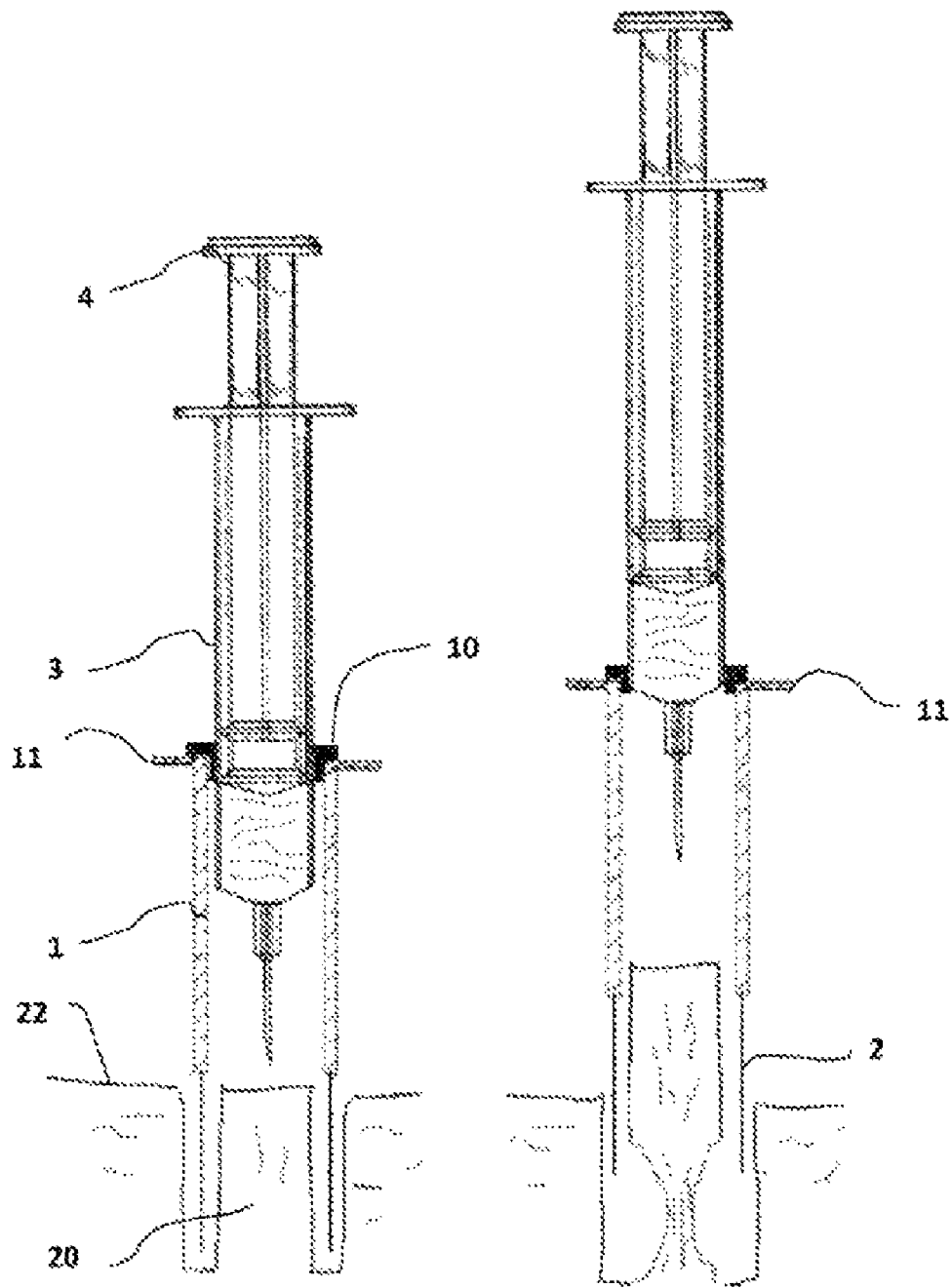
FIGS. 3A and 3B show a cross sectional view of exemplary sequence of steps for the biopsy procedure, according to one embodiment.

According to one aspect of the invention, at the proximal end of the barrel a circular seal 10 is mounted on the proximal edge of the sleeve and is in frictional engagement with the outside wall of the barrel (FIGS. 3A and 3B). The seal is preferably made from rubber. Despite the frictional engagement the sleeve is able to slide smoothly through and out of the barrel. This allows the barrel to be present in close contact with the seal and assures air tight engagement similar to the stopper 8 inside the barrel. In one variation, the instrument has the means for releasable retaining the blade in certain locations relative to the barrel as will be explained later.

To perform the procedure, the sleeve 1 is first retracted to expose the needle 6. After injecting the anesthetic fluid, the sleeve is extended to cover the needle and expose the blade 2. The sleeve (not the barrel) can then be held and used as a biopsy instrument pressing it against the skin 22 perpendicularly and twisting it back and forth around its axis until it cuts through the tissue as shown in FIG. 3a.

Afterwards for the purpose of cutting the base of the tissue without the need for additional instruments and without pulling the instrument out, the barrel is retracted further proximally to create a negative pressure while the blade is kept inside the tissue. This holds the skin plug 20 inside the blade and stabilizes it for cutting the base as shown in FIG. 3b. This also can be accomplished by retracting the plunger 9 of the syringe. The instrument is then lifted up by holding the sleeve and with a bending and twisting movement the skin tissue can be completely severed from the base. Finally, the biopsy, now stuck inside the blade can be expelled into a container by pressing either the plunger or the sleeve down (not shown in figures).

In a variation of the method used to cut the skin from its base, the sleeve is brought back to its resting position exposing the needle again. The needle then can be used to pierce the base of the specimen and lift it up away from the skin. It then can be completely severed by the advancing the blade again through the specimen (not shown in figures).

In one variation, a circular rim 11 is mounted on the proximal end of the barrel to aid in securing the negative pressure inside the sleeve (FIGS. 3A and 3B). Since the barrel tends to resist retraction when creating the negative pressure, it would be desirable to lock it at that point before it slides back into the sleeve and release the pressure. This can be accomplished by holding the barrel with the thumb and index finger at a point close to the rim. The instrument can then be pulled out and with a bending and twisting motion the tissue can be cut from its base. This versatile locking means is better than having a fixed locking means, since the point at which maximal negative pressure is different from one biopsy location to another.

Figure 4A:
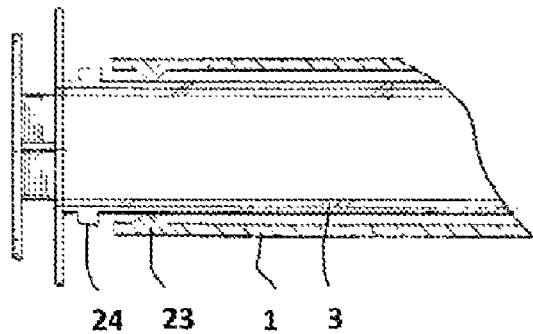
FIG. 4A shows a partial cross sectional view of one implementation with projections 23 mounted inside the sleeve that engage collars 24 on the syringe, to lock the instrument in a retracted position.
Figure 4B:
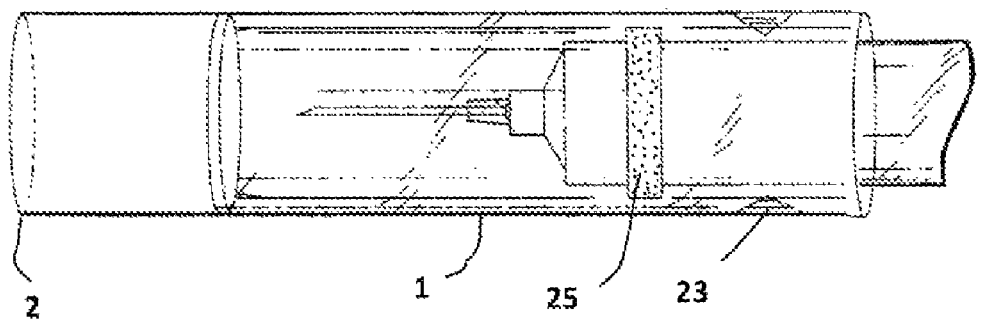
FIG. 4B shows a partial perspective view of one implementation with projections 23 mounted inside the sleeve that engage collars 25 on the syringe, to lock the instrument in an extended position.

Now referring to FIGS. 4a and 4b, in a variation of the previous embodiment a plurality of juxtaposed projections 23 are present on the inside surface of the sleeve at the proximal end. Preferably, they are sloped in both directions forming a triangular shape with an apex at the middle. The axis of the projections is parallel with the long axis of the sleeve. They are to engage two collars 24 and 25 at the outside surface of the barrel 3. Preferably, the collars are located in two positions, at each extreme end of the barrel. The collars represent a uniform round elevation from the outside surface of the barrel. Whenever the projections meet one of the collars they end up in a frictional engagement. This is a locked position for the sleeve to allow for either injecting anesthesia in one engagement to cutting the tissue in the other engagement. In both engagements, the friction can be overcome with manual force.

Other means for locking the sleeve relative to the barrel can also be employed. Such ways may include (but are not limited to) maneuvers and parts such as using springs, using switches, rotating the barrel relative to the sleeve or using projections that have shapes that complement or dock into collars. Furthermore, rather than having a cylindrical sleeve that holds the blade, arms can be used to project the blade beyond the needle. Preferably, the needle should lie in the central axis of the blade's circumference, but another location is sideways, at the same plane that the blade's wall occupy, by introducing a tiny perpendicular gap through the wall, small enough to allow the needle without jeopardizing the ability of the distal sharp edge to cut through the skin (not shown in figures).

Preferably, both the sleeve and the syringe are made of transparent material to view the amount of fluid injected. Other means for sliding the sleeve relative to the barrel can also be employed such as a spring loaded mechanism or a twisting action of the sleeve. It is possible in one variation to add markers on the side of the sleeve (not shown in figures) corresponding to the desired depth of the biopsy to aid the surgeon while cutting the tissue and knowing when to stop. Although the current trend employs disposable punches and syringes, where the instrument is manufactured with the anesthetic fluid and shipped, the instrument can also be reused by replacing the needle and/or the barrel and sterilizing the punch.

Figure 5:
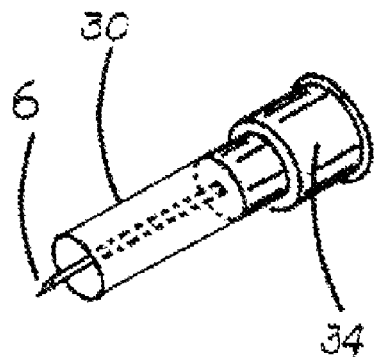
FIG. 5 shows an exemplary perspective view of one device according to one aspect of the invention.

In another preferred embodiment, rather than having the blade slidable and movable by the sleeve, the blade 30 is fixed to the base of the needle hub 34 (FIG. 5). The needle assembly depicted in the figure is detachable and is fixed to syringes by tight engagement. The needle 6 lies at the centre of the blade and is hidden within the blade except for its distal end which projects beyond the distal edge of the blade. The length of the exposed part of the needle that lies beyond the edge of the blade should not exceed 6 mm. This will ensure that the needle can be used to inject the anesthetic without going too deep. Various methods of attachment known in the industry field can be used for fixing the blade to the hub such as welding, gluing or making the both parts as one piece from the outset. The hub's base can be enlarged to accommodate larger blades. When performing the biopsy, the injection is given normally, and then the blade is urged into the tissue with a twisting motion until it cuts through. The needle being in a central position will not interfere with the procedure and may actually help in lifting the tissue for cutting the base. The same concept can also be employed on fixed non-detachable needles.

In all of the previous embodiments, larger hubs can be used for larger biopsies and different variations of the needle assemblies can be used. In disposable instruments with a premade anesthetic (no need to withdraw anesthetic before procedure), permanently fixed needles are preferred. However other variations include detachable hubs, or a Luer lock type of needles. Furthermore, detachable needle assemblies can be fitted frictionally (as shown in FIGS. 1 and 2) or by twisting or screwing it to the distal tapered end of the barrel.

Depending on the type of the needle assembly, the anesthetic fluid can be withdrawn just before using the instrument or it can be prepared at the time of manufacturing the instrument to save time before the procedure. Since all biopsies have to be performed after injecting an anesthetic, it would be desirable to have a premade anesthetic inside the punch-syringe to reduce the number of needle waste and therefore cutting down on the cost and time of the procedure. Safety syringes that have needles that snap inside the barrel after use can be also used as a punch syringe where rather than having the blade move the needle is withdrawn inside to expose the blade.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

What is claimed is:

1. A biopsy instrument for harvesting one or more skin biopsies, comprising:
    a syringe assembly having a barrel in fluid communication with a needle, and a plunger slidably positioned in the barrel;
    a sleeve slidably coupled to and at least partially housing the barrel, wherein the inner diameter of the sleeve is greater than the outer diameter of the barrel; and
    a cylindrical blade coupled to the distal end of the sleeve, the cylindrical blade configured to harvest cylindrical skin biopsies;
    wherein the sleeve is longitudinally slidable relative to the barrel, between a first position where the blade is retracted and the needle exposed, and a second position where the blade is extended and the needle is retracted within the sleeve.

2. The biopsy instrument of claim 1, further comprising a locking mechanism that is configured to lock the sleeve relative to the barrel at the first position and the second position.

3. The biopsy instrument of claim 2, wherein the locking mechanism comprises: a projection mounted inside the sleeve; a first collar mounted on the proximal end of the outside wall of the barrel; a second collar mounted on the distal end of the outside wall of the barrel; and wherein the projection is configured to be in frictional engagement with the first collar at the first position and wherein the projection is configured to be in frictional engagement with the second collar at the second position.

4. The biopsy instrument of claim 1, further comprising an air-restricting seal disposed between the sleeve and the barrel.

5. The biopsy instrument of claim 1, further comprising a circular rim mounted on a proximal end of the barrel, configured to secure negative pressure inside the sleeve.

6. The biopsy instrument of claim 1, wherein the barrel contains an anesthetic solution.

7. The biopsy instrument of claim 1, wherein the blade is configured to harvest skin biopsies with a diameter ranging from 1-8 mm.

8. The biopsy instrument of claim 1, wherein the blade is configured to harvest skin biopsies having a thickness ranging from 2-20 mm.

9. The biopsy instrument of claim 1, wherein the needle is configured to inject an anesthetic fluid into a patient.

10. A method for harvesting a skin biopsy from a patient, comprising the steps of:
    providing a biopsy instrument comprising:
        a syringe assembly having a barrel in fluid communication with a needle, and a plunger slidably positioned in the barrel;
        a sleeve slidably coupled to and at least partially housing the barrel; and
        a cylindrical blade coupled to the distal end of the sleeve, wherein the inner diameter of the sleeve is greater than the outer diameter of the barrel;
        wherein the sleeve is longitudinally slidable relative to the barrel, between a first position where the blade is retracted and the needle exposed, and a second position where the blade is extended and the needle is retracted within the sleeve;
    retracting the sleeve to expose the needle;
    injecting an anesthetic fluid into the patient with the needle;
    removing the needle from the patient;

extending the sleeve to advance the blade;

pressing and rotating the blade against and through the skin to cut a cylindrical skin biopsy;

cutting the base of the skin biopsy; and removing the skin biopsy from the patient.

11. The method of claim 10, wherein the step of cutting the base of the skin biopsy further comprises the step of:

generating a negative pressure to hold the skin biopsy inside the blade.

12. The method of claim 11, wherein the negative pressure is generated by retracting the barrel away from the skin while the blade is inside the skin.

13. The method of claim 11, wherein the negative pressure is generated by retracting the plunger while the blade is inside the skin.

14. The method of claim 10, wherein harvesting a skin biopsy is accomplished without the need for additional instruments.

* * * * *